United States Patent [19]

Lindsay et al.

[11] Patent Number: 4,789,467
[45] Date of Patent: Dec. 6, 1988

[54] AUTOMATED DISINFECTION SYSTEM

[75] Inventors: Edward R. Lindsay, Clearwater; Robert C. Kusmierczyk; Norman F. Cameron, both of St. Petersburg, all of Fla.

[73] Assignee: Baxter Travenol Laboratories, Inc., Deerfield, Ill.

[21] Appl. No.: 858,437

[22] Filed: Apr. 30, 1986

[51] Int. Cl.⁴ .............................................. B01D 13/00
[52] U.S. Cl. ................................... 210/103; 210/120; 210/136; 210/140; 210/321.69; 210/321.71; 422/113; 422/116
[58] Field of Search ..................... 210/136, 140, 321.3, 210/234, 235, 321.69, 321.71, 143, 120, 103, 134, 105; 134/169 C, 166 C, 100, 57 R; 422/116, 112, 113

[56] References Cited

U.S. PATENT DOCUMENTS 4,158,034 6/1979 Riede et al. ..................... 210/321.69
4,166,031 8/1979 Hardy .............................. 210/140 X
4,332,264 6/1982 Gortz et al. ..................... 210/321.69

OTHER PUBLICATIONS

DePalma, J. R. et al, "New Artificial Kidney Reuse Machine", Tran. Am. Soc. Artif. Int. Organs, vol. 20, 4/1974, pp. 584–588.

"Travenol Introduces the Automated Disinfection Module", brochure no. 466720, Travenol Laboratories, Inc., 12/85.

"Umbrellas", brochure no. SMYK980, Vernay Laboratories, Inc., 2 pages, 1980.

Primary Examiner—Richard V. Fisher
Assistant Examiner—Linda S. Evans
Attorney, Agent, or Firm—Paul C. Flattery; Charles R. Mattenson; Macdonald J. Wiggins

[57] ABSTRACT

An automated disinfection system for a hemodialysis machine having a proportioning pump includes a manifold block having a check valve for connection to a container of disinfection solution. The manifold block has an outlet connected to the suction line of the pump and an inlet connected to a warm water source via a solenoid valve. A timing and control circuit controls the solenoid valve to produce a water rinse cycle when the solenoid valve is open and a disinfection cycle when the solenoid valve is closed. The check valve closes when positive pressure is present in the manifold block during a rinse cycle and opens to admit solution to the pump when negative pressure is present in the manifold block during a disinfection cycle.

12 Claims, 5 Drawing Sheets

FIG. 1

PRIOR ART

AUTOMATED DISINFECTION SYSTEM

BACKGROUND OF THE INVENTION

1. Field of the Invention

The present invention relates to cleaning and disinfecting of a hemodialysis machine, and more particularly to an automated system therefor.

2. Description of the Prior Art

Hemodialysis machines are utilized by persons having insufficient or inoperative kidney functions. The machines may be used at a health facility or in the patient's home. The machine attaches the patient through an extracorporeal circuit of blood tubing to a dialyzer having a pair of chambers separated by a thin semipermeable membrane. The patient's blood is circulated through one of the chambers. The hemodialysis machine maintains a constant flow of a dialysate through the second chamber. Excess water and wastes from the blood are removed by ultrafiltration through the membrane and carried out by the dialysate to a drain.

A typical hemodialysis machine provides a pair of hoses which connect to the dialyzer and include a source of incoming water, a filter and heater for bringing the water to a required temperature, a source of a dialysate which is introduced into the water in a predetermined concentration and necessary pumps, pressure regulators, a deaerator, flow controllers and regulators. When the machine is in use, the hoses are connected to the inlet and outlet ports of the dialyzer. After use, the hoses are removed from the dialyzer and connected to a bypass which couples the two hoses together. It is then necessary to clean the dialysate from the machine and the various tubes, hoses and other elements and to disinfect the various lines and parts of the machine.

Typical chemicals used for disinfection and cleaning are a 5.25% concentrated sodium hypochlorite solution, commonly referred to as "bleach", and a 37% formaldehyde solution, commonly referred to as "Formalin$^R$". In the cleaning and disinfecting procedure, it is necessary to first rinse the machine lines and parts with water to remove the dialysate and thereafter to cause either the bleach or formaldehyde to pass through the machine for predetermined times. After the disinfection operation, the solution must be thoroughly flushed out by means of a post-rinse.

Both of these chemicals are hazardous to the patient and the operator must be extremely careful not to inadvertently dialyze with either of these two chemicals remaining in the system. Although some apparatus may have safety devices which require certain conductivity of the dialysis, there are occasions in which improper concentrations have been used and serious injury or death to a patient has occurred.

A typical prior art procedure for disinfection will be described using a hemodialysis machine available from Travenol Laboratories, Inc. of the SPS 450 series. In this machine, an external line known as the concentrate line is normally connected to a source of dialysate concentrate which is mixed with the incoming warm water by means of a proportioning pump to produce the required dialysate solution. When the machine is to be cleaned and disinfected, the concentrate line is removed from the dialysate concentrate container and connected to a water rinse port of the machine. The hoses to the dialyzer are disconnected therefrom and connected together through a bypass or interlock port. The machine is operated for a preselected rinsing period which cases the incoming water to be circulated through the concentrate line, the proportioning pump, and the other lines and elements of the machhine which flushes the dialysate out through the drain.

After the required prerinsing period, the operator now introduces the bleach or formaldehyde solution. Generally, this material is poured into an open cap. About 140–160 mls of the material is required. The operator removes the concentrate line from the water rinse port and drops the end thereof into the cup. The machine is then operated for a specified disinfect period during which the proportioning pump draws the bleach or formaldehyde from the cup and introduces it into the water circulating through the system. The proportioning will be the same as that for which the proportioning pump is set for dialysis; for example, a ratio of 34 parts of water to one part of concentrate is commonly used. The operator must be careful to determine when the container of bleach or formaldehyde is nearly empty since the drawing of air into the machine is undesirable.

After passing a preselected volume of bleach or formaldehyde through the system for the selected period of time, the concentrate line is again connected manually to the water rinse port and the machine is operated in a post-rinse mode using water to thoroughly flush out all of the disinfecting liquid. When using bleach, which is essentially a cleaning procedure, the post-rinse can follow immediately after the treatment with the disinfect cycle. However, the procedure requires that formaldehyde be ingested into the machine, the machine turned off and stored within the system for at least two hours. In general practice, the use of formaldehyde is limited to the last operation of the day with the apparatus and the formaldehyde allowed to stand in the machine overnight. After the formaldehyde storage period, the post water rinse is accomplished to remove the residual formaldehyde. Some users will have apparatus to test the residual formaldehyde until it is less than about 10 parts per million.

As will be recognized, a significant amount of labor is required on the part of the operator to perform a disinfection procedure. The operator must monitor the apparatus and, since some of the periods require 10 to 30 minutes, there is a significant cost for this labor. Furthermore, the handling of these relatively dangerous materials in open containers provides several opportunities for spillage, which can be dangerous to the operator and can produce undesirable fumes. If the proper rinse times and storage times are not strictly observed, there is always the danger of leaving residual bleach or formaldehyde in the system such that a risk exists with respect to the next patient undergoing dialysis on the machine.

As may be recognized, there is a long felt need for an automated hemodialysis machine cleaning and disinfecting system that will automatically and accurately time the cycle of events, that will obviate the need for open containers, that will reduce the labor required for the operation, and that will increase the safety of the process. Furthermore, such a system would perform its function in a more uniform manner, with more predictable results, and eliminate the potential for disinfectant to be introduced into the machine during dialysis.

SUMMARY OF THE INVENTION

The present invention is a system that can be applied to a hemodialysis machine and which, once started, will automatically carry out the disinfection cycles with minimum human intervention. An electronic timing module is provided which is preferably controlled from the proportioning pump of the machine to accurately control the volume of bleach or formaldehyde used in the procedure. The proportioning pump also is used to time the pre-rinse and post-rinse cycles. The invention eliminates the use of open cup containers by providing a special bottle which can be filled at a bench and a vent cap placed thereon. The bottle includes a built-in syphon outlet having a special gooseneck coupling tip. The control module includes a recess having a labyrinth-type check valve into which the coupling tip is inserted. This construction eliminates dripping or spilling of solutions when installing and removing bottles since there are no hoses or connectors hanging loose from the bottles. The container is supported by the module with the coupling tip in a position to permit the solution in the container to be drawn into the machine at the proper time. The labyrinth check valve is a part of a manifold block attached to the control module. The syphon arrangement and the labyrinth valve provide an air wash through the valve prior to flow of the disinfection solution for removing any residual previous solution. The manifold block and control module are preferably mounted to the side of the hemodialysis machine.

In addition to the manifold block, an air vent valve, a solenoid valve, and a check valve are installed in the dialysate circuit of the hemodialysis machine. These elements are controlled as will be described below by the electronic module and the conditions of the water flow in the machine.

As discussed above, the concentrate line from the proportioning pump which normally draws a dialysate concentrate into the dialysate loop or circuit is connected via a rinse port through the manifold block to a normally open solenoid valve into the dialysate circuit. Briefly, during the period in which the bleach or formaldehyde is to be ingested into the machine, the control module operates the solenoid valve, disconnecting the concentrate line from the warm pressured water and permitting the proportioning pump to draw the solution from the container into the proportioning pump. During an appropriate time, which may be on the order of 10-12 minutes, the disinfection solution is continuously drawn into the dialysate line, passed therethrough and disposed of through the drain outlet from the machine. The exact time based on the capacity of the proportioning pump and the time required to ingest the desired volume of solution. Prior to the disinfect cycle just described, the pre-rinse cycle operates with the normally open solenoid valve opened. Thus, the positive water pressure closes the labyrinth-type check valve and only warm water is passed through the system to achieve the desired rinsing of the dialysate from the last use thereof. Similarly after the disinfection cycle, the control module again permits the solenoid valve to open and the labyrinth-type valve to close due to the water pressure, again circulating water through the system to flush out the bleach or formaldehyde as the case may be.

The vent valve mentioned above is a safety device and is connected at the water inlet point of the dialysate circuit and is operated by water pressure existing at the vent valve. When such pressure is present, the vent valve is closed. The vent valve seat is connected to the manifold block via an umbrella or flap-type valve within the block. When the vent valve is closed, the umbrella valve cannot be opened by negative pressure in the manifold block and no venting takes place. As a safety feature, if the water supply should be turned off or momentarily interrupted, which under certain circumstances might permit drawing of bleach or formaldehyde into the dialysate circuit during operation of the machine, the vent valve would be open and negative pressure in the manifold block would cause the umbrella valve to open, venting the proportioning pump concentrate line to the atmosphere and preventing any solution from the container from being drawn into the circuit.

It is therefore a principal object of the invention to provide an automated disinfection system applicable to hemodialysis machines to permit the required cycles of rinse and disinfection to occur automatically once initiated with minimum human intervention.

It is another object of the invention to provide an automatic disinfection system for hemodialysis machines which obviates the requirement for open containers, for manual connection and disconnection of lines, and for manual timing of cycles.

It is still another object of the invention to provide an automatic disinfection system for hemodialysis machines which will eliminate objectionable fumes, spilling of disinfection solutions and the like and which includes safety features to eliminate the possibility of contamination of dialysate with disinfection solutions.

It is yet another object of the invention to provide a syphon-type container for disinfection solutions which will eliminate dripping and spilling of solutions and which will leave only small residual amounts when the container is removed.

It is a further object of the invention to provide a labyrinth check valve at the disinfection solution input of the system which in conjunction with the syphon-type container will provide an air wash to remove residual amounts of solutions prior to introduction of a different solution.

These and other objects and advantages of the invention will become apparent from the following detailed description when read in conjunction with the drawings.

DETAILED DESCRIPTION OF THE PREFERRED EMBODIMENT

The invention is a system added to a hemodialysis machine to automatically perform the water rinses and disinfection required after each use of the machine. Before describing the invention, it is pertinent to briefly describe a typical hemodialysis machine and the prior art manual process which the invention supplants.

Figure 1:
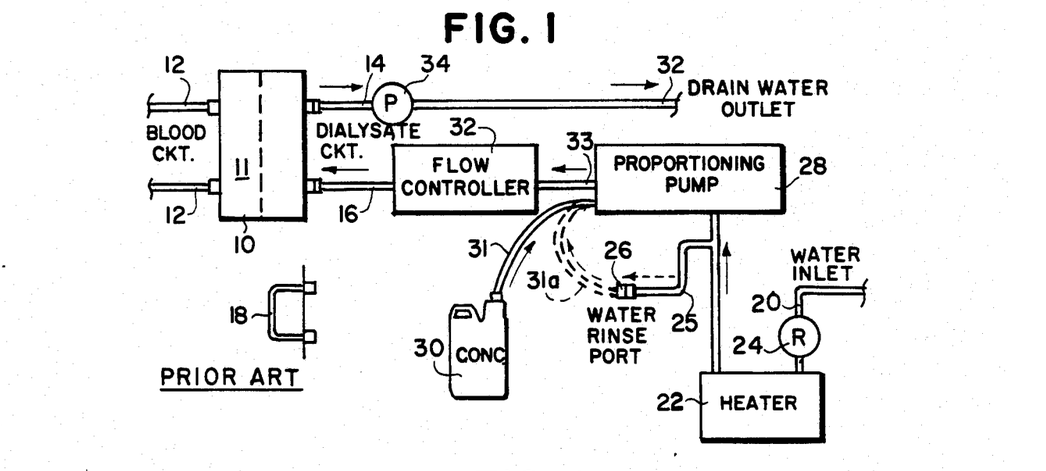
FIG. 1 is a simplified block diagram of a prior art hemodialysis machine.

FIG. 1 shows a simplified block diagram of a typical hemodialysis machine known in the prior art such as the Travenol SPS 450 with a number of ancillary elements omitted for clarity. A dialyzer 10 includes a semi-permeable membrane 11. Tubing 12 connected to one chamber of dialyzer 10 is connected to a blood circuit including a blood pump and associated accessories which attach to the patient to circulate the patient's blood through the chamber. The dialysate chamber on the other side of membrane 11 is connected via hoses 14 and 16 to the hemodialysis machine. The dialysate circuit of the machine is connected to a water inlet by line 20 via pressure regulator 24 from which water flows to heater 22 for raising the incoming water to a required temperature. The warm water flows to proportioning pump 28 which has an inlet connected to concentrate line 31 and an output line 33. During dialyzing, proportioning pump 28 draws in measured amounts of dialysate concentrate via concentrate line 31 which is added to the water in a preselected ratio into output line 33. A concentrated dialysate solution is provided in a container 30 to which concentrate line 31 is connected. As proportioning pump 28 operates, it will draw concentrate from container 30 and inject it into the water flowing through the pump such that the specified concentration solution is output on line 33. tyically, a 34–1 dilution of the concentrate will occur, although any desired ratio may be used. The dialysate is then circulated via flow controller 32 to the dialyzer 10 via hose 16. After absorbing the excess water and impurities from the patient's blood via membrane 11, the dialysate is returned to the machine via hose 14. Pump 34 assists in circulating the dialysate to a drain water outlet 38.

After use of the hemodialysis machine, the dialysate circuit must be rinsed and disinfected. The procedure involves disconnecting hoses 14 and 16 from dialyzer 10 and connection thereof to bypass 18. Concentrate hose 31 is removed from container 30 and connected to the water rinse port 26 which is normally closed. However, when concentrate line 31 is connected thereto as indicated by the dashed lines 31a, the water rinse port 26 is opened and warm water will flow via line 25 and through line 31a into proportioning pump 28 as indicated by the dashed arrows upon the suction stroke of the pump.

As will now be recognized, operation of the machine and the dialysate circuit with this configuration will cause the warm water instead of concentrate to be pumped through the system and will rinse out the dialysate.

As previously discussed, to manually disinfect the system, line 31a is disconnected from water rinse port 26 and connected to a source of bleach or formaldehyde. The operator then must monitor the system while the bleach or formaldehyde is being circulated through the system. After the prescribed amount of solution has been pumped through the system, the line 31a must again be connected to the water rinse port 26 and a post rinse accomplished.

Figure 2:
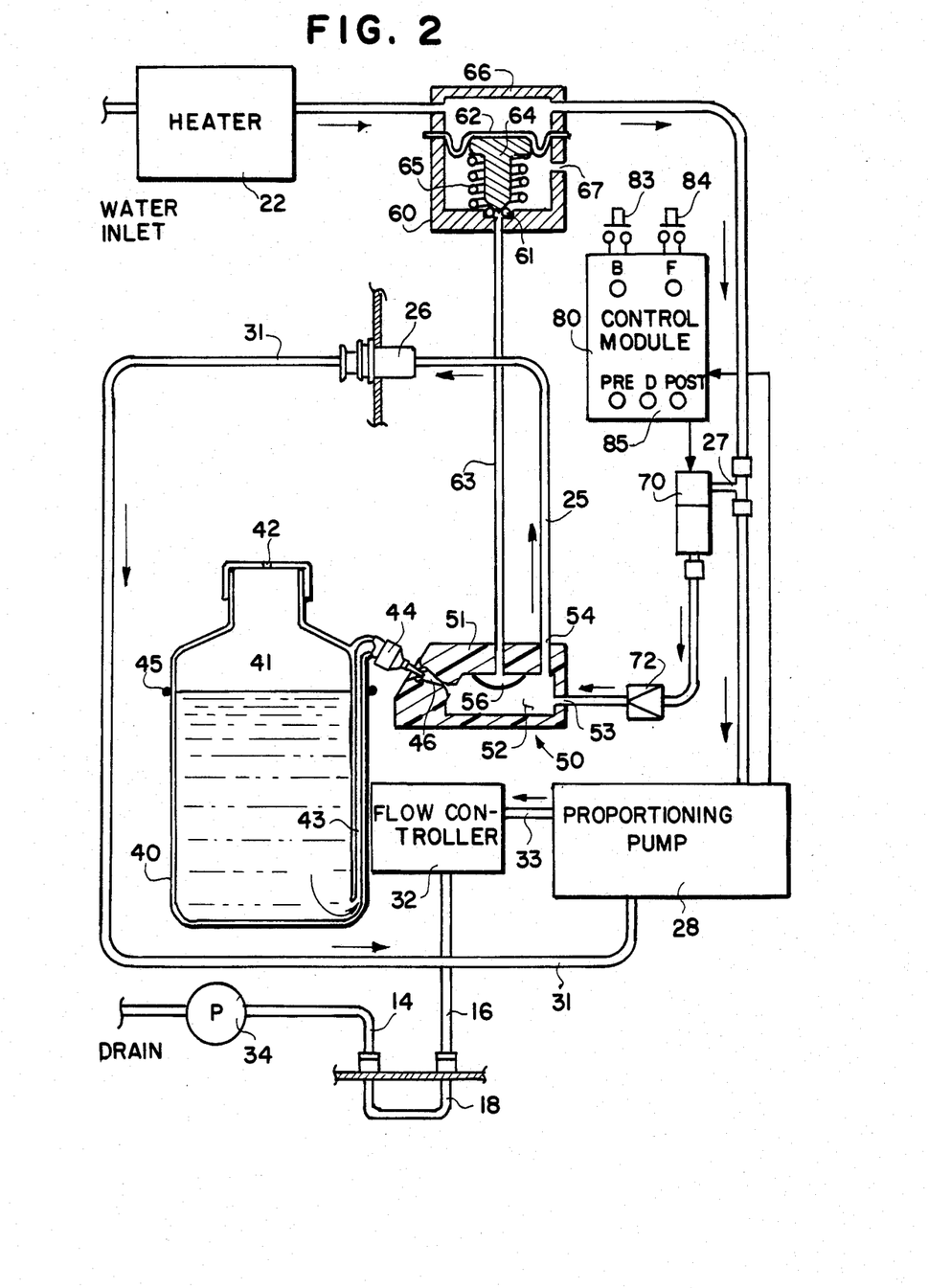
FIG. 2 is a schematic diagram of the automatic disinfection system of the invention installed in the hemodialysis machine of FIG. 1.

Turning now to FIG. 2, a simplified portion of the hemodialysis machine described in FIG. 1 is shown with the elements of the invention added thereto. It will be noted that concentrate line 31 from proportioning pump 28 is connected to water rinse port 26 and remains connected for the entire rinsing and disinfecting operation. Water rinse port 26 is connected to an outlet 54 in manifold block 50. Manifold block 50 includes a chamber 52 and has an input 53 connected via a check valve 72 to normally-open solenoid 70. As may be noted, solenoid 70 is connected to tee 27 in the water input line to proportioning pump 28. As will be recognized, tee 27 was originally connected to water rinse port 26 in the exemplary prior art machine of FIG. 1. Thus, in accordance with the invention, normally-open solenoid valve 70, check valve 72, and manifold block 50 are inserted between port 26 and tee 27.

Manifold block 50 includes a body 51 and an input check valve 46 preferably of the labyrinth type disposed in body 51. Valve 46 will be described in more detail hereinafter. Manifold block 50 also includes a vent line 63 which is normally closed by umbrella valve 56. Umbrella valves 6 is a type of flap valve which will open under very small negative pressure in chamber 52. Vent line 63 is connected to a vent valve 60 which includes diaphragm 62, valve element 64, valve seat 61 and spring 65. Valve element 64 which will be normally held open by spring 65 seats in valve seat 61 which may include an O-ring type seal. When water pressure is present in the valve chamber 66, valve element 64 is forced downward by diaphragm 62, sealing valve seat 61. In this condition, it will be noted that umbrella valve 56 will remain closed. If the water pressure is disconnected or cut off for any reason, spring 65 will open valve seat 61 and this will open vent line 63 to the atmosphere through vent opening 67 in vent valve 60. As will be discussed hereinafter, the system operation will cause umbrella valve 56 to open if there is negative pressure in chamber 52 and water pressure is lost, which vents chamber 52 of manifold block 50 to the atmosphere via vent valve 60.

Figure 3:
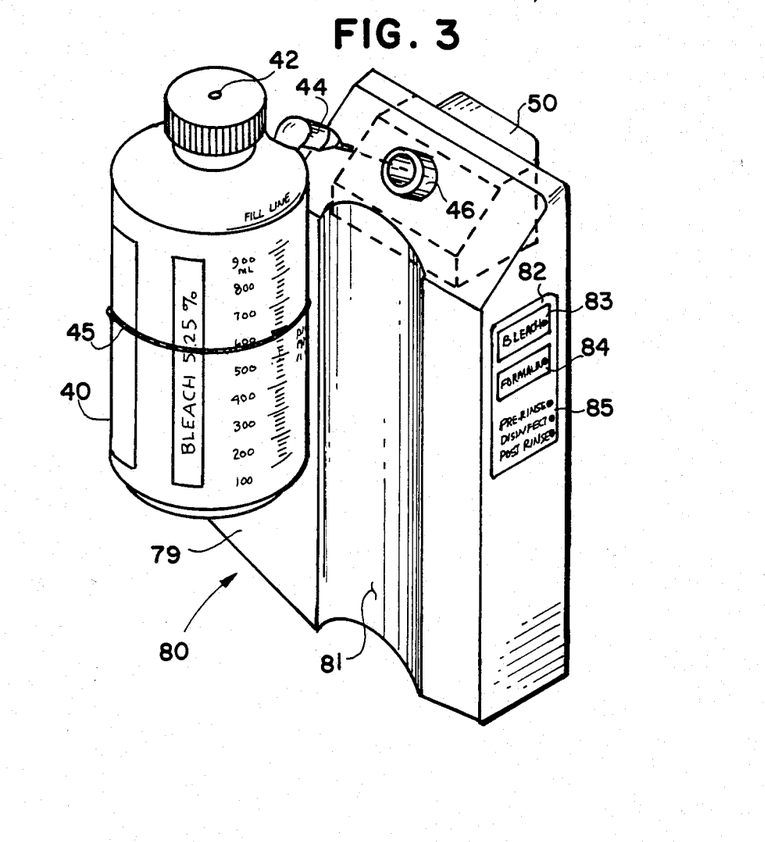
FIG. 3 is a perspective view of the control module of the invention showing the manner of installing a disinfection container.

Referring now to container 40 shown in cross-sectional view, this container is preferably a rigid wall plastic container with a cap having vent 42 therein. Container 40 is filled with the solution 41, such as bleach or formaldehyde, to be used for the disinfection process. Preferably, container 40 will include scale markings on the external wall thereof. An O-ring or similar band 45 may be installed around container 40 to indicate the level at the start of the procedure so that the amount of ingested solution after a procedure can be verified. A syphon leg 43 is provided which is preferably molded into the sidewall of container 40. The gooseneck and coupling tip 44 are provided at the upper end of syphon tube 43. Referring to FIG. 3, a perspective view of a preferred arrangement of manifold block 50 and container 40 is shown. The control circuits are preferably contained in module block 80 having manifold block 50 mounted at the upper end thereof. Module housing 79 includes a recessed area 81 having a similar curvature as container 40. To install a container of solution 40, the coupling tip 44 is inserted into labyrinth check valve 46 which is a portion of manifold block 50. Container 40 is preferably formed from a rigid plastic having sufficient strength that the syphon leg and coupling tip will support the container which nests in recess 81. When the container 40 is not plugged into valve 46, valve 46 is closed to positive pressure inside of chamber 52. When container 40 is plugged into valve 46, a negative pressure in chamber 52 as caused by closing of solenoid valve 70 will cause the fluid in container 40 to be drawn up via syphon tube 43 and to flow into chamber 52. However, at any point when a positive pressure occurs in chamber 52, valve 46 will close. Details of valve 46 will be shown hereinbelow.

It is a required operating procedure for the user to install a container 40 only when the clearing and disinfecting procedure is to be accomplished. After completion of such a procedure, container 40 is to be removed as a safety measure. As will be shown later, if container 40 is left in place inadvertently, its contents cannot be drawn into a dialysate during operation of the machine.

Figure 4:
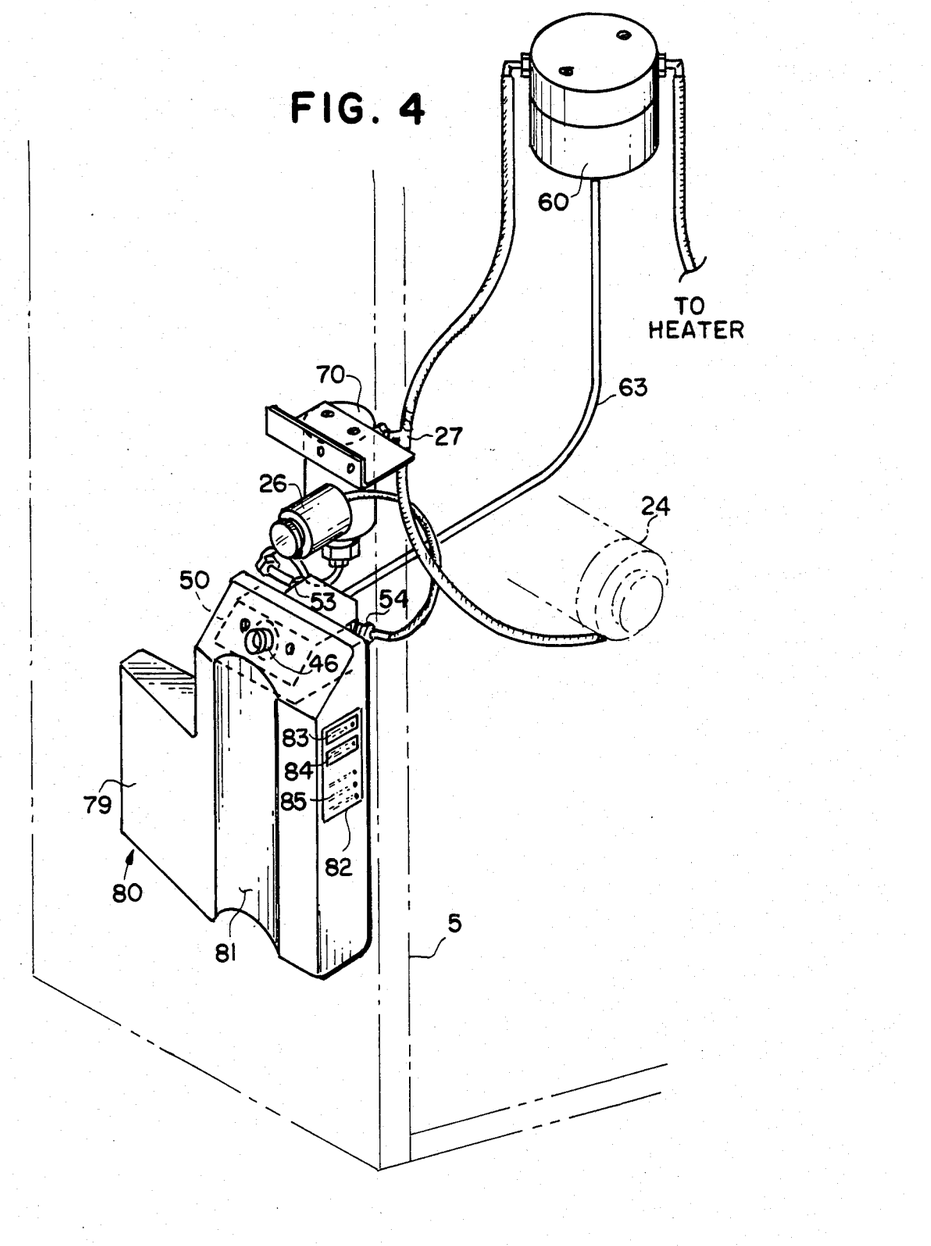
FIG. 4 is a perspective view of the elements of the invention installed on a Travenol hemodialysis machine partly shown in phantom view.

An installation of elements of the system in a Travenol Model SPS 450 hemodialysis machine is shown in FIG. 4. Solenoid valve 70 is mounted by means of a bracket, inside of cabinet 5 just above the water rinse port as shown in phantom view 26. Module housing 79 is attached to the side of cabinet 5 just below water rinse port 26 so as to be convenient for the operator to install the container 40 and also to permit relatively short additional lines to be added to the machine. Vent valve 60 is mounted in the line from tee 27 to the heater. As best seen in FIG. 3, the mode of operation of the automated disinfection system is indicated by a panel 82 on the side of module block 80. Panel 82 includes two membrane-type pressure switches, bleach switch 83 and formaldehyde switch 84. The operator presses the appropriate switch when initiating a cycle of operation. LED's behind the membrane switches indicate which one is in use. Similarly, the timing operation performed by control module 80 is indicated by LED's 85 to indicate whether the unit is in the pre-rinse cycle, the disinfect cycle, or the post-rinse cycle.

Figure 5:
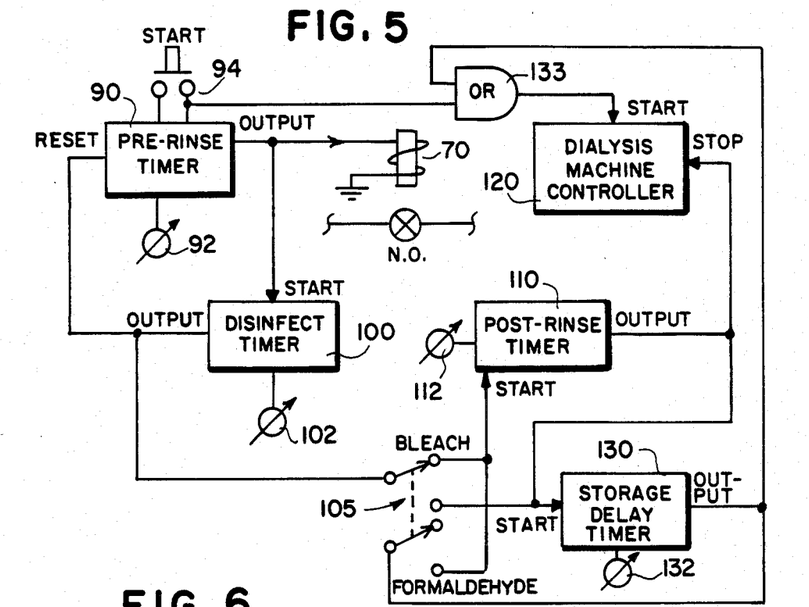
FIG. 5 is a simplified block diagram of a typical control circuit for the invention.

FIG. 5 shows a simplified block diagram of a timing and control circuit in accordance with the invention. The timing system includes a pre-rinse timer 90 which has an adjustment 92 for selecting the desired pre-rinse cycle time. A start button 94 is provided which initiates the sequence. Push button 94 starts the operation of timer 90 and also controls the dialysis machine controller 120 to start the operation of the pumps of the machine. Pre-rinse timer 90 is preferably an electronic timer; however, a mechanical timer may also be used. As will also be understood by those of skill in the art, a microprocessor may be provided and programmed to perform the required control functions.

The output from timer 90 is connected to the solenoid of normally open solenoid valve 70. When timer 90 completes its timing period, the output will operate solenoid valve 70, closing the valve. Thus, during the pre-rinse period, valve 70 is opened and water circulates through manifold block 50 and line 31 into the inlet of proportioning pump 28. When timer 90 completes its timing cycle, the connection between tee 27 and inlet 53 of manifold block 50 is closed. Negative pressure from proportioning pump 28 on line 31 will then cause the disinfectant solution 41 in container 40 to be drawn into chamber 52 of manifold block 50 and then via water rinse port 26 and line 31 into proportioning pump 28.

When pre-rinse timer 90 has completed its cycle, the output therefrom starts disinfectant timer 100 which is adjustable to a desired timing period (by adjustment 102). For the selected period of timer 100, the disinfectant solution will be drawn through the dialysate lines and out the drain therefrom. When disinfect timer 100 completes its timing period, its output is connected to reset pre-rinse timer 90 which will remove the output therefrom, permitting solenoid valve 70 to release and open. This places positive pressure in chamber 52 of manifold block 50 from the incoming water pressure and causes labyrinth check valve 46 to close, thereby halting the ingestion of the disinfecting solution. At this point, water again will circulate through the dialysate lines and out through the drain. As previously mentioned, when bleach is being used during the disinfect cycle, it is desirable to immediately rinse the bleach out of the system at the end of the disinfect cycle. A switch 105 is shown in FIG. 5 in the BLEACH position. Thus, the output from disinfect timer 100 will also start post-rinse timer 110 having an adjustment 112. The machine will continue on its post-rinse cycle until timer 110 times out, at which point the output thereof is applied to the STOP control for dialysis machine controller 120. This action will stop the pumps and other elements of the dialysis machine after completion of the post-rinse cycle.

In the event that formaldehyde is being used as a disinfectant, switch 105 will be in the FORMALDEHYDE position. When disinfect timer 100 times out in this instance, its output will start a storage delay timer 130 which can be adjusted by adjustment 132. The output from disinfect timer 100 will also, in this condition, stop the dialysis machine controller, shutting off the pumps. This permits the formaldehyde solution to remain in residence in the lines and elements of the dialysate lines. When storage delay timer 130 times out, it will restart the dialysis machine and, via switch 105, also start post-rinse timer 110. This initiates the post water rinse which will be halted when post-rinse timer 110 times out since its output stops dialysis machine controller 120.

Where there may be differences in the desired cycle times between a bleach cycle and a formaldehyde cycle, switch 105 may include additional contacts which can automatically set timing controls 92, 102, and 112 as desired.

Figure 6:
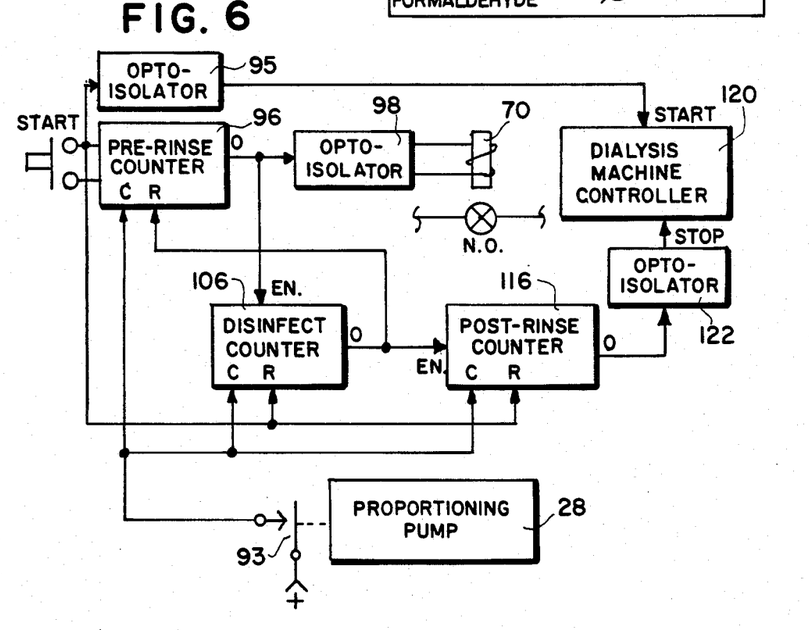
FIG. 6 is a simplified block diagram of an alternative control system for the invention.

In FIG. 6 is shown a preferred control circuit for use with the invention. This circuit makes use of the fact that proportioning pump 28 operates on a volume basis and is a piston pump which measures the concentrate as it is ingested into the water line. Therefore, as the pump completes right and left strokes, it is essentially metering the volume of fluid going through the machine. These pump strokes are activated electrically by a magnet which activates a low voltage circuit via a magnetic read switch which in turn activates a solid state relay controlling solenoid valves to control the mechanical valving of the pump. The circuit shown in simplified form in FIG. 6 uses proportioning pump 28 with a contact 93 which is operated on each stroke of the pump. Contact 93 therefore produces a low voltage pulse which is utilized to advance counters. A pre-rinse counter 96 is used with a suitable start switch which enables the counter.

In the Travenol hemodialysis machine being used as an example of the application of the invention, it has been found that a pre-rinse time of 11 minutes is sufficient. With the proportioning pump 28 used in the Travenol apparatus, nine left and right strokes will occur in 11 minutes when pump 28 is set for a dialysate flow rate of 500 ml/min. Therefore, counter 96 is set to produce an output after nine counts. The use of a digital counter for this purpose is preferable which may be set for any desired count as will be understood by those of skill in the art. The logic output from pre-rinse counter 96 is applied to an optoisolator 98 connected to operate normally open solenoid valve 70 as described with respect to FIG. 5. The output signal is also applied to disinfect counter 106 to enable that counter. When disinfecting with either bleach or formaldehyde, it has also been found that 11 minutes is sufficient. Therefore, disinfect counter is set to count nine left and right strokes of the pump 28. At the ninth count, a logic output from counter 106 will reset pre-rinse counter 96, causing solenoid valve 70 to release and open. As will now be recognized, this begins the post-rinse cycle. A suitable post-rinse time for use with bleach has been determined to be 22 minutes which is equivalent to 18 right and left strokes. Therefore, post-rinse counter 116 is set to count to 18 before producing a logic signal on its output line. This output signal operates optoisolator 122 which stops the dialysis machine controller 120.

When using formaldehyde as a disinfectant, 33 minutes has been determined to be a satisfactory time for that cycle and corresponds to 27 left and right strokes of proportioning pump 28. Although not shown in FIG. 6, a selection switch and storage delay counter may also be included as in FIG. 5 to permit selection of either bleach or formaldehyde for the system cycle.

Figure 7:
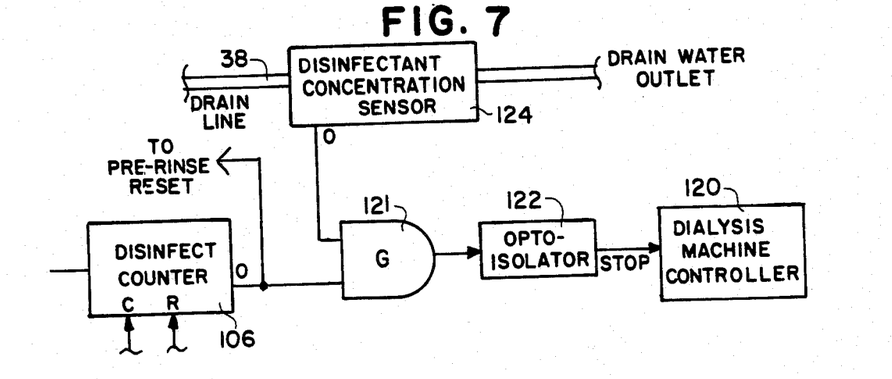
FIG. 7 is a simplified block diagram of a control system of the invention utilizing a sensor.

An alternative arrangement for the post-rinse cycle control is shown in FIG. 7 where the dialysis machine includes a disinfectant concentration sensor. The sensor may be installed in drain line 38 and adapted to produce a logic output when the concentration of disinfectant is less than a predetermined level. An AND gate 121 has an input connected to receive the logic signal from sensor 124 and also to receive the logic output from disinfect counter 106. A logic signal will be received from counter 106 when solenoid valve 70 opens. Upon indication of sufficient post-rinse by a logic output from sensor 124, gate 121 will be enabled and a logic signal to optoisolator 122 will stop the dialysis machine controller cutting off the system. Thus, the system is sensitive to the concentration of disinfectant rather than a fixed post-rinse time.

Figures 8, 9:
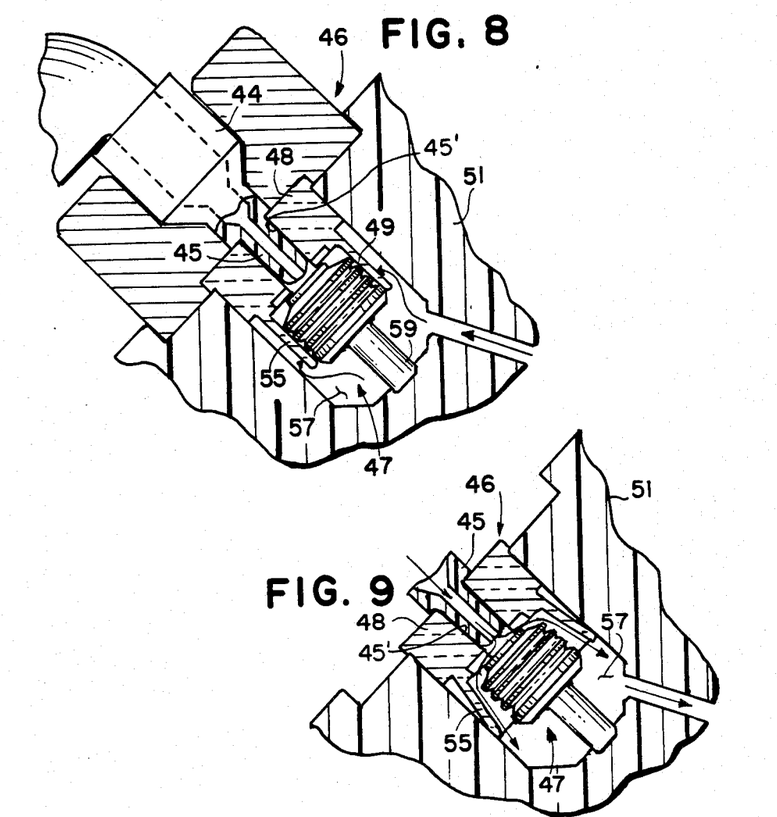
FIG. 8 is a cross-sectional view of the labyrinth valve of the invention in its closed position.
FIG. 9 is a cross-sectional view of the valve of FIG. 8 in its open position.

Turning now to FIGS. 8 and 9, a description of the novel labyrinth check valve used in the invention will be given. FIG. 8 shows a partial cross-sectional view of manifold block body 51 and labyrinth check valve 46. Body 51 of manifold block 50 is preferably formed from plastic such as acrylic. A cylindrical bore 57 is provided into which a rubber valve cylindrical element having a body portion 48 and a sleeve or skirt element 55 is inserted. The valve element is preferably formed from a soft butyl rubber, although other suitable materials may be used. Sleeve portion 55 extends inward from body portion 48. A central bore 45' is provided in body portion 48 which is slightly smaller than tip 45 of container connector tip 44 such that the tip forms a tight fit when container 40 is installed therein. A plastic plug element 47 is provided having a body portion 49 comprised of a plurality of triangular lands and indentations therearound. The body portion 49 fits snuggly into the valve sleeve or skirt 55 and a spacing pin 59 projects from the body portion and fits into a recess in bore 57.

The operation of the valve 46 as a check valve is indicated in FIG. 8 in which it is assumed that a positive pressure exists in chamber 52 of the manifold block 50. As indicated by the arrows in FIG. 8, this pressure is incident on the outer surface of sleeve or skirt 55 forcing the soft rubber material thereof tightly against the lands in body portion 49. Thus, there can be no flow of air or liquid in this direction.

Turning to FIG. 9, operation of valve 46 in the open condition is shown. When negative pressure is present in chamber 52 of manifold block 50, there will be a suction applied to the outer surfaces of valve sleeve 55 and, due to atmospheric pressure at the inlet of connector tip 45, the skirt will be forced outward permitting a flow of air or liquid as shown by the direction of the arrows.

As will be discussed hereinafter, it is also important that a greater negative pressure will be required to operate valve 46 than to open umbrella valve 56. The tension to be overcome in opening valve 46 may be controlled to some extent by the diameter of the body portion 49 of valve plug 47. When this portion is slightly greater in diameter than the interior diameter of the valve sleeve 55 and is inserted into sleeve 55, it will preload the valve due to the hoop strength of the sleeve 55. Another advantage of valve 46 is that any kind of particulate in the fluid which is flowing therethrough tends to be deposited in the grooves as the fluid washes across the lands of the body which prevents such material from interfering with sealing of the valve.

The design of labyrinth valve 46 and container 40 solves a problem of residual solutions which may be left in the valve upon removal of container 40. Since bleach and formaldehyde will react violently if brought together, such action could occur if, for example, a bleach disinfection is later followed by a formaldehyde disinfection and a drop or two of bleach were left in valve 46. When the formaldehyde solution container is first installed, air must be drawn from syphon leg 43 before the syphon starts. This air washes any residual bleach solution into chamber 52 of manifold block 50 which will be drawn by pump 28 into the warm water. When the formaldehyde reaches valve 46, there will be no mixing of solutions.

Having disclosed the elements and interconnection of the elements of the invention, the process of operation of the invention will now be discussed in more detail. Referring to FIG. 2, it will be assumed that the hemodialysis machine has been used with a patient and has been disconnected and is ready for disinfection. The operator connects hoses 14 and 16 to the bypass 18 which is a part of the Travenol machine. The concentrate line 31 is removed from the concentrate source and connected to water rinse port 26. At this point, the system is connected as shown in FIG. 2. A bottle or container 40 of the desired disinfectant material is obtained and connector tip 44 is inserted into check valve 46. The container 40 will nest within recess 81 and is self-supporting when so installed. Assuming for example that the container contains bleach, the bleach control button 83 on control model 80 is depressed starting the pre-rinse timer. The dialysis machine controller is simultaneously energized, operating pumps 28 and 34. Water is assumed to be available at the water inlet and passes through heater 22 and regulator 24 into vent valve 60. The positive pressure in chamber 66 forces valve core 64 against valve seat 61 sealing vent line 63. The water flows via tee 27 to proportioning pump 28. Since solenoid valve 70 is opened, water also flows through tee 27 in the direction of the arrows in FIG. 2 via check valve 72 into chamber 52 of manifold block 50. Since there is positive pressure at this point in chamber 52, check valve 46 will remain closed. Similarly, umbrella valve 56 will be closed. Therefore, warm water will flow out of port 54 through line 25, out water rinse port 26 and, via concentrate line 31, back to proportioning pump 28 and be drawn into the pump during its intake stroke. This water will rinse dialysate concentrate from these lines as well as from the proportioning pump internal passages. The water from line 31 and directly from the heater flows out of proportioning pump 28 through flow controller 32, thereby rinsing hoses 16 and 14. The rinse water then drains out via pump 34.

When the bleach control button 83 was depressed, the timing cycle began. Upon completion of the timing cycle, the control module 80 causes solenoid valve 70 to be operated closing valve 70 and preventing water flow into manifold block 50. However, since proportioning pump 28 is operating, suction via concentrate line 31 and line 25 will create a negative pressure in chamber 52. As previously described, this negative pressure will cause valve 46 to open and produce a negative pressure in syphon line 43. The atmospheric pressure via vent 42 on the bleach solution 41 will cause the bleach to flow up syphon line 43 as indicated by the arrow in FIG. 2 and into manifold 50. When syphon line 43 is filled, the flow is aided by the syphoning action. Advantageously, when container 40 is later removed from module block 80, the syphon leg 43 will be drawn back into the container liquid 41 and only a minute amount of solution will be left in valve 46. This feature also eliminates dripping or spilling of the solution during removal and handling of the container 40.

Solenoid valve 70 being closed at this point prevents any flow of bleach solution into tee 27 and, as a safety factor, check valve 72 would block any tendency of such flow in the event that solenoid valve 70 failed. Thus, the bleach solution pulled into chamber 52 is drawn into proportioning pump 28 as indicated by the flow arrows. It is mixed with the incoming warm water in the proportions for which the pump is set, and in this example, dilutes the bleach solution by 34–1. The bleach solution then passes through flow controller 32 to disinfect hoses 16 and 14 and is thereafter dumped via the drain. The bleach also disinfects the passages in proportioning pump 28.

The timer in control module 80 controls valve 70 to maintain it in the closed position during the duration of the disinfecting cycle. When this timer times out, the control module releases solenoid valve 70, causing it to open. This permits water to flow from tee 27 via solenoid valve 70 and check valve 72 into chamber 52 producing a positive pressure therein and closing labyrinth valve 46. The warm water is again directed via line 25 and concentrate line 31 to the proportioning pump 28 which draws the warm water into the pump. This action continues for the selected post-rinse time period to rinse out the bleach solution from the lines and passages. Upon completion of this timed cycle, the control module 80 will turn off the proportioning pump 28 and pump 34 and the disinfection operation is complete. The operator will then remove container 40 for storage until it is again needed.

As previously mentioned, it has been found that about 120–140 mls of disinfectant solution is satisfactory. A container 40, which may hold about 1 liter, may therefore be used for a number of operations without the necessity for refilling and advantageously limits the handling of disinfectant solutions and reduces the risk of spillage which can be irritating to skin and otherwise undesirable.

As previously mentioned, the system of the invention includes certain devices which provide a safety factor in its operation. For example, when container 40 is in place and a rinse cycle is in effect, it is seen that the positive pressure of water in chamber 52 closes valve 46 and prevents any of the disinsfectant to be drawn into the system. However, if during the post-rinse cycle, the water pressure should be turned off or momentarily fail, proportioning pump via concentrate line 31 and line 25 would put a negative pressure in chamber 52. This could cause bleach or formaldehyde solution to be drawn into the chamber and into proportioning pump 28. If this occurred near the end of the post-rinse cycle, the apparatus would shut down shortly thereafter and there is a chance that disinfectant could be left in the proportioning pump to flow controller and hoses 14 and 16. Thus, when the machine was used for the next patient, this would contaminate the dialysate and pose a risk to the patient.

To prevent this from happening, vent valve 60 is utilized. If the water pressure should fail at any time, spring 65 will open valve seat 61 by raising the valve element 64. This permits atmospheric pressure via vent opening 67 to be present in vent line 63. The suction from proportioning pump 28 placed in chamber 52 will cause umbrella valve 56 to open, venting the chamber to the atmosphere. As previously mentioned, umbrella valve 56 will open at a much less negative pressure than labyrinth valve 46. Therefore, labyrinth valve 46 will remain closed and no disinfectant can be ingested into the apparatus.

As will now be recognized, an automated disinfection system for a hemodialysis machine has been disclosed. In its most elementary aspect, the invention utilizes a normally open solenoid valve in combination with a manifold to first control a warm water rinse cycle to rinse dialysate from the machine, to thereafter switch to a disinfect cycle to pass a disinfection solution through the machine, and to thereafter switch to a warm water rinse cycle to rinse the solution from the machine.

The manifold permits the disinfection solution container to be connected through a check valve into the manifold. The manifold is connected to the warm water line by the solenoid valve and to the suction line of a proportioning pump in the machine. Thus, opening the solenoid valve places positive pressure in the manifold from the water line which closes the check valve resulting in warm water flowing into the pump suction line. However, when the solenoid valve is closed, negative pressure from the suction line causes the check valve to open, drawing disinfection solution into the pump for circulation through the machine.

A timing and control system has been disclosed to produce the required rinse and disinfect cycles.

Although a specific embodiment of the invention has been described, it is to be understood that such embodiment is for exemplary purposes only and various modifications may be made without departing from the spirit and scope of the invention. While the description applies to a particular hemodialysis machine, the invention may be used with other models and brands of machine.

We claim:

1. An automated disinfection system for installation in a hemodialysis machine, said machine having a proportioning pump with a water inlet means, a suction inlet means and an outlet means connected to a dialysate system, said disinfection system comprising:

a vent valve having a flow path between means defining a water source and said water inlet of said proportioning pump, said vent valve including a housing having a vent chamber and means defining a vent opening to atmospheric pressure and a valve seat, said valve seat having a biased valve body associated therewith, said valve body attached to a diaphragm disposed in said housing, said diaphragm defining said flow path and said vent chamber, said valve body closing said valve seat only when water under pressure is present in said flow path;

a remote operated valve having an inlet means connected to said water inlet of said proportioning pump and a water outlet means;

a manifold block having means defining a chamber, a vent line communicating with said manifold chamber and connected to said valve seat of said vent valve, a disinfectant output line from said manifold chamber connected to said suction inlet of said proportioning pump, and a disinfectant input connection communicating with said manifold chamber;

a check valve disposed in said disinfectant input connection of said manifold block, said check valve permitting flow of disinfectant only into said manifold chamber;

a container for a disinfectant concentrate solution, said container having an output connector inserted into said disinfectant input connection of said manifold block; and control means operatively connected to said remote operated valve for sequentially opening same to water rinse said dialysate system, and closing said remote operated valve to disinfect said dialysate system.

2. In a hemodialysis machine having means defining a source of water under pressure, a proportioning pump having an inlet means connected to said source and an outlet means connected to a dialysate line system, and a suction line, wherein the improvement comprises:

a manifold block having an outlet means connected to said suction line, a first inlet means and a second inlet means;

a check valve connected to said first inlet and having an input connection to means defining a source of disinfection solution, said check valve opening under negative pressure in said manifold block and closing under positive pressure in said manifold block;

a remote controlled valve connected between said water source and said second inlet; and control and timing means connected to said remote controlled valve for selectively opening said remote controlled valve, said proportioning pump drawing water via said suction line into said dialysate line system, and said control and timing means selectively closing said remote controlled valve, such that said proportioning pump draws a disinfection solution via said suction line to disinfect said dialysate line system.

3. In a hemodialysis machine having means defining a source of incoming water, a heater for heating incoming water, a proportioning pump having an inlet means connected to receive heated water from said heater, a suction input means and an outlet means, a water rinse port, and dialysate lines connected to said proportioning pump outlet, wherein the improvement comprises:

manifold means having means defining a chamber, said chamber having an inlet means and outlet means, said chamber outlet connected to said water rinse port;

a control valve connected between said heated water inlet of said proportioning pump and said chamber inlet;

check valve means disposed in said manifold means and communicating with said chamber, said check valve means having an external fluid inlet means;

output container means for holding a disinfection concentrate solution and having an outlet connector connected to said external fluid inlet of said check valve means, said check valve means for permitting flow of fluid only from said container means into said chamber;

a line connected from said suction input of said proportioning pump to said water rinse port; and timing and control means connected to sequentially open said control valve for a first preselected time period for circulating heated water by said proportioning pump through said dialysate lines, to close said control valve for a second preselected time period for circulating said concentrate solution and heated water through said dialysate lines, and to open said control valve for a third preselected time period for circulating heated water through said dialysate lines.

4. The improvement as defined in claim 3 in which said normally open valve means comprises a normally open solenoid operated fluid valve in which energizing said solenoid closes said solenoid valve.

5. The improvement as defined in claim 3 in which said check valve includes:

a valve body having means defining a cylindrical bore therein;

a cylindrical valve body element formed from a soft pliable material disposed in said cylindrical bore and having a first input passage means therethrough;

a soft resilient cylindrical sleeve portion extending inwardly from said body element;

a cylindrical plug element tighty disposed within said sleeve element, said plug element having means defining a plurality of lands and indentations therearound; and a second output passage means of said check valve means from said cylindrical bore through said valve body to said chamber of said manifold means.

6. The improvement as defined in claim 5 in which said container includes:

a vented cap;

a syphon leg molded into the side wall of said container and communicating with the interior thereof;

a gooseneck at the upper end of said syphon leg; and a coupling tip disposed on said gooseneck and communicating with said syphon leg, said coupling tip formed to mate with said first passage of said check valve.

7. The improvement as defined in claim 6 in which said container is formed from rigid plastic.

8. The improvement as defined in claim 3 which further comprises:

(a) a vent valve having means defining a water chamber portion connected to said source of water, said vent valve means including:

(i) a housing, (ii) a valve seat in said housing having a valve body disposed therein for opening and closing said valve seat, (iii) a diaphragm in said housing connected to said valve body and defining said water chamber, (iv) a biasing means to maintain said valve body in a normally open position, (v) an atmospheric vent opening means in said housing communicating with said valve seat when said valve seat is open, and (vi) said valve seat being closed by said diaphragm when water pressure exists in said water chamber and opened by said biasing means when no water pressure is present in said water chamber;

(b) a vent input means to said chamber of said manifold means, said vent input connected to said valve seat; and (c) umbrella valve means disposed in said manifold chamber for closing said vent input thereto when a positive pressure is present in said manifold chamber and for opening said vent input when a negative pressure is present in said manifold chamber.

9. The improvement as defined in claim 3 in which said timing and control means includes:

a pre-rinse timer having an output means operatively connected to said control valve, said pre-rinse timer opening said control valve at the beginning of said first time period and closing said control valve means at the end of said first time period;

a disinfect timer coupled to said output of said pre-rinse timer to start said disinfect timer to produce said second time period, said disinfect timer having an output means connected to said pre-rinse timer to reset said pre-rinse timer at the end of said second time period; and a post-rinse timer connected to the output of said disinfect timer and started at the end of said second time period by said disinfect timer, said post-rinse timer defining said third time period, and having an output means operatively connected to said control valve for opening said control valve at the end of said second time period and connected to said hemodialysis machine to stop the operation of said proportioning pump at the end of said third time period.

10. The improvement as defined in claim 9 further including means for adjusting each of said pre-rinse timer, said disinfect timer and said post-rinse timer.

11. The improvement as defined in claim 9 in which said proportioning pump is a piston pump and includes pulse generating means to produce a low voltage pulse on each stroke thereof;

said pre-rinse timer includes a first counter means connected to said pulse generating means to produce said first time period;

said disinfect timer includes a second counter means connected to said pulse generating means to produce said second timer period; and said post-rinse timer includes third counter means connected to said pulse generating means to produce said third time period.

12. The improvement as defined in claim 11 which further comprises:

a storage delay timer connected to the output of said disinfect timer which is started at the end of said second time period by said disinfect timer, in which said disinfect timer output is connected to said hemodialysis machine to stop said proportioning pump, said storage delay timer defining a fourth time period, and having an output means connected to said hemodialysis machine to start said proportioning pump.

* * * * *